US010577584B2

(12) United States Patent
Velthuis et al.

(10) Patent No.: US 10,577,584 B2
(45) Date of Patent: Mar. 3, 2020

(54) PHOTODYNAMIC PROCESS AND PRODUCT OBTAINED THEREFROM

(71) Applicant: KIADIS PHARMA INTELLECTUAL PROPERTY BV, Amsterdam-Duivendrecht (NL)

(72) Inventors: Jurjen Velthuis, Amsterdam-Duivendrecht (NL); Liesbeth De Jong, Amsterdam-Duivendrecht (NL); Manfred Rudiger, Amsterdam-Duivendrecht (NL)

(73) Assignee: KIADIS PHARMA INTELLECTUAL PROPERTY BV, Amsterdam-Duivendrecht (NL)

( * ) Notice: Subject to any disclaimer, the term of this patent is extended or adjusted under 35 U.S.C. 154(b) by 49 days.

(21) Appl. No.: 15/551,572

(22) PCT Filed: Feb. 19, 2016

(86) PCT No.: PCT/EP2016/053561
§ 371 (c)(1),
(2) Date: Aug. 16, 2017

(87) PCT Pub. No.: WO2016/131960
PCT Pub. Date: Aug. 25, 2016

(65) Prior Publication Data
US 2018/0044630 A1 Feb. 15, 2018

(30) Foreign Application Priority Data
Feb. 19, 2015 (EP) .................... 15155755

(51) Int. Cl.
C12N 5/00 (2006.01)
C12N 5/0783 (2010.01)
A61K 41/00 (2006.01)
A61K 35/17 (2015.01)

(52) U.S. Cl.
CPC ............ *C12N 5/0087* (2013.01); *A61K 35/17* (2013.01); *A61K 41/0057* (2013.01); *C12N 5/0636* (2013.01)

(58) Field of Classification Search
CPC ............... C12N 5/0087; C12N 5/0636; C12N 2501/999; A61K 41/0057; A61K 35/17
See application file for complete search history.

(56) References Cited

U.S. PATENT DOCUMENTS

2006/0088507 A1   4/2006  Roy

FOREIGN PATENT DOCUMENTS

| EP | 0773794 B1 | 6/2001 |
| WO | WO98/03224 | 1/1998 |
| WO | WO01/24824 | 4/2001 |
| WO | WO02/079183 | 10/2002 |

OTHER PUBLICATIONS

International Search Report dated Apr. 25, 2016 for International Application No. PCT/EP2016/053561.
Brasseur et al., "Eradication of Multiple Myeloma and Breast Cancer Cells by TH9402-mediated Photodynamic Therapy: Implication for Clinical Ex Vivo Purging of Autologous Stem Cell Transplants," *Photochemistry and Photobiology*, 72(6):780-787 (Jan. 2000).
Mielke et al., "A clinical-scale selective allodepletion approach for the treatment of HLA-mismatched and matched donor-recipient pairs using expanded T lymphocytes as antigen—presenting cells and a TH9402-based photodepletion technique," *Blood*, 111(8):4392-4402 (Apr. 15, 2008).
Perruccio et al., "Photodynamic purging of alloreactive T cells for adoptive immunotherapy after haploidentical stem cell transplantation," *Blood Cells, Molecules, and Diseases* 40(1):76-83 (Jan.-Feb. 2008).
Belikov, V.G., "Pharmaceutical Chemistry, In Two Parts, Part 1. General Pharmaceutical Chemistry", 1993, pp. 43-47.

*Primary Examiner* — Taeyoon Kim
(74) *Attorney, Agent, or Firm* — One LLP

(57) ABSTRACT

The present invention relates to a method for ex vivo photodynamic treatment of cells. A cell preparation is incubated in a first medium having 5 μM or less of a photosensitive compound. A population of cells in the cell preparation retains the photosensitive compound, for example, a salt of 2-(4,5-dibromo-6-amino-3-imino-3H-xanthen-9-yl)-benzoic acid methyl ester. The first medium is then replaced with an extrusion medium to remove the photosensitive compound. The cell preparation is then illuminated in the extrusion medium to selectively kill the population of cells retaining the photosensitive compound, thereby creating an illuminated cell preparation.

14 Claims, No Drawings

PHOTODYNAMIC PROCESS AND PRODUCT OBTAINED THEREFROM

CROSS-REFERENCE TO RELATED APPLICATIONS

This is a national stage application of International Application No. PCT/EP2016/053561, filed Feb. 19, 2016, published as WO 2016/131960 A1, entitled "Improved Photodynamic Process and Product Obtained Therefrom," which in turn claims priority to European Application No. 15155755.0, filed Feb. 19, 2015. All of the above applications are expressly incorporated herein by reference in their entirety for all purposes.

FIELD OF THE INVENTION

The present invention relates to a photodynamic process and product obtained therefrom. In particular, it relates to a photodynamic process used for the depletion of certain cells from a cell population and to the product obtained therefrom.

BACKGROUND OF THE INVENTION

Transplantations or allografting involves the donation of material from one individual or multiple individuals, the donor(s), to another individual, the recipient. During allografting, donor cells may react to recipient cells and tissue (graft-versus-host disease), which is an unwanted reaction due to a mismatch in HLA antigens. There are several methods to identify and eliminate donor cells, typically T-lymphocytes, which react to and are activated by recipient cells. The mixed lymphocyte reaction is an ex vivo method which can be used to study the reactivity between host and donor cells. In combination with photodynamic therapy it can be used to selectively eliminate donor cells which are activated by host cells.

Such a combined identification and elimination of alloreactive T-cells is used for the manufacture of T-cell enriched donor lymphocyte preparations selectively depleted of alloreactive T-cells towards the host. This is e.g. described in WO 01/24824 where these preparations are manufactured by mixing donor cells with γ-irradiated recipient cells in the presence of IL-2 to induce a one-way MLR of the donor cells in the direction of the recipient's mismatched major HLA-antigens. After culture period, the cells are harvested and exposed to a fluorescent photosensitive rhodamine compound, TH9402, which accumulates in all cells. After a subsequent period of incubating the cells in culture media without the presence of TH9402, the dye is preferably retained in those cells that were activated in the one-way MLR, i.e. those donor cells that reacted to the recipient's mismatched HLA-antigens. Next, the cells are exposed to light of a visible wavelength, leading to activation of TH9402 and generation of highly cytotoxic reactive oxygen radicals, thereby eliminating those donor cells that reacted to the recipient's mismatched HLA-antigens but sparing the other donor cells. Mielke et al. (2008) Blood 111: 4332-4402 describes an MLR in which expanded T-cells, generated using anti-CD3 and Il-2, are co-cultured with responder cells from HLA-matched or -mismatched donors. In this study, incubations with 7.5 micromolar TH9402 give significantly better results than incubations with 5 micromolar. Perrucio et al. (2007) Blood Cells Molecules and Diseases 40: 75-83 describes an MLR process followed by photodynamic treatment with no extrusion step. Ninety to ninety-five percent of the cell population dies.

A major limitation of the method is the number of cells that can be handled within a single treatment. The concentration of cells to be treated cannot exceed one million cells/ml in the extrusion phase without compromising the quality of the final product. Therefore, in order to treat more cells one would need to increase the volume to be handled in the process. Yet, working with large volumes, e.g. one liter and larger, is difficult and impacts the robustness and reproducibility of the treatment. Photodynamic treatment of sufficient cells for one patient would require about ten illumination devices or several rounds of treatment.

DETAILED DESCRIPTION OF THE INVENTION

The present invention relates to a photodynamic process comprising
(i) incubating a cell preparation in a medium comprising 5 micromolar or less of a photosensitive compound;
(ii) replacing the medium of (i) with an extrusion medium to remove photosensitive compound and
(iii) illuminating the cell preparation in the extrusion medium to selectively kill those cells which have retained the photosensitive compound.

One advantage of the process according to the invention is that smaller volumes and higher cell concentrations may be used in the extrusion phase than conventionally used in a reference process using more than 5 micromolar photosensitive compound, e.g. 10 micromolar, without compromising the quality of the final product. Surprisingly, the cell product obtainable by this process is improved in comparison to a reference cell product obtainable or obtained by a reference process using more than 5 micromolar photosensitive compound, e.g. 10 micromolar photosensitive compound. Another advantage is that more cells may be treated photodynamically at the same time and under the same conditions. Yet another advantage is that less photosensitive compound may be used, while obtaining a cell product which is improved in comparison to the reference cell product. All these advantages have a huge impact on standardization and on the efficiency and ease of handling. The state of the art methods only allow photodynamic treatment in low concentrations, e.g. $1 \times 10^6$ cells/ml. If an illumination device is used which can handle e.g. $100 \times 10^6$ cells per experiment, treating $1 \times 10^9$ cells in total, which is an average amount of cells for one person, would require ten rounds of $100 \times 10^6$ cells or the employment of ten illumination devices at the same time. Treatment conditions between rounds of treatment may differ slightly and therefore several rounds of treatment are preferably avoided. Using ten illumination devices for one treatment is also costly and space consuming and is therefore also preferably avoided. Using the method according to the invention, it is possible to treat $1 \times 10^9$ cells in higher concentrations and smaller volumes. As a consequence, the number of illumination devices may be reduced by 80% to one or two and all cells may be treated at the same time and under the same conditions. The method according to the invention leads to the cell concentration in the extrusion phase to be higher than in the coloration phase. This allows for important medium reduction, facilitates scalability and allows for processing more cells with equal devices.

In the photodynamic process according to the invention, the photosensitive agent may be used to selectively kill certain cells. In one embodiment, this is achieved because the photosensitive compound accumulates in all cells, but after a wash step is preferentially retained in certain cells, which allows for the selective killing of specific cells. In another embodiment, the photosensitive compound accumulates in certain cells only, which allows for the killing of these cells only.

The term 'photodynamic process' refers to a process in which a photosensitive compound is exposed to light and thereby converted into one or more products which are cytotoxic. Any suitable photosensitive compounds may be used in the process according to the invention, including rhodamines and rhodamine derivatives. Of particular interest are the rhodamine derivatives disclosed in WO 02/079183, which are covered by formula (I)

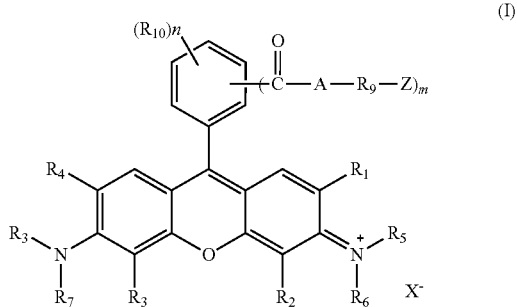

wherein:
  one of $R_1$, $R_2$, $R_3$, $R_4$ and $R_{10}$ represents an halogen atom and each of the remaining $R_1$, $R_2$, $R_3$, $R_4$, and each of the remaining $R_{10}$ group is independently selected from the group consisting of hydrogen, halogen atoms, an amino, acylamino, dialkylamino, cycloalkylamino, azacycloalkyl, alkylcycloalkylamino, aroylamino, diarylamino, arylalkylamino, aralkylamino, alkylaralkylamino, arylaralkylamino, hydroxy, alkoxy, aryloxy, aralkyloxy, mercapto, alkylthio, arylthio, aralkylthio, carboxyl, alkoxycarbonyl, aryloxycarbonyl, aralkoxycarbonyl, carbamoyl, alkylcarbamoyl, dialkylcarbamoyl, cyano, hydroxysulfonyl, amidosulfonyl, dialkylamidosulfonyl, arylalkylamidosulfonyl, formyl, acyl, aroyl, alkyl, alkylene, alkenyl, aryl, aralkyl, vinyl, alkynyl group and by the corresponding substituted groups;
  m=0-1;
  n=1-4
  A is nil, O, or NH;
  $R_3$ represents an alkylene group;
  Z is H, amino, dialkylamino, or trialkylamino salt;
  X− is an anion; and
  $R_5$, $R_6$, $R_7$ and $R_8$ are independently H or C1-C6 alkyl or $R_1$ in combination with $R_5$ or $R_6$, or $R_2$ in combination with $R_5$ or $R_6$, or $R_3$ in combination with $R_7$ or $R_8$, or $R_4$ in combination with $R_7$ or $R_8$ represents an alkylene; and the rhodamine derivatives disclosed in EP 0 773 794. In particular dibromorhodamine derivatives are of interest.

Suitable photosensitive compounds include photosensitive rhodamine derivatives which are salts of 2-(4,5-dibromo-6-amino-3-imino-3H-xanthen-9-yl)-benzoic acid methyl ester; 2-(4,5-dibromo-6-amino-3-imino-3H-xanthen-9-yl)-benzoic acid ethyl ester; 2-(4,5-dibromo-6-amino-3-imino-3H-xanthen-9-yl)-benzoic acid octyl ester; 2-(4,5-dibromo-6-amino-3-imino-3H-xanthen-3-yl)-benzoic acid n-butyl ester; 2-(6-ethyl amino-3-ethyl imino-3H-xanthen-9-yl)-benzoic acid n-butyl ester; 2,7-dibromorhodamine B methyl ester; 2,7-dibromorhodamine B hexyl ester; 4,5-dibromorhodamine 6G; 2'-(6-dimethylamino-3-dimethylimino-3H-xanthen-9-yl) 4',5' dichloro-benzoic acid methyl ester; 4,5-dibromorhodamine 110 2-(2-methoxy ethoxy) ethyl ester or rhodamine B 3-bromopropyl ester; such as for example photosensitive rhodamine derivative selected from the group consisting of hydrobromide or hydrochloride salts of 2-(4,5-dibromo-6-amino-3-imino-3H-xanthen-9-yl)-benzoic acid methyl ester; hydrobromide or hydrochloride salts of 2-(4,5-dibromo-6-amino-3-imino-3H-xanthen-9-yl)-benzoic acid ethyl ester; hydrobromide or hydrochloride salts of 2-(4,5-dibromo-6-amino-3-imino-3H-xanthen-9-yl)-benzoic acid) octyl ester; hydrobromide or hydrochloride salts of 2-(4,5-dibromo-6-amino-3-imino-3H-xanthen-9-yl)-benzoic acid) n-butyl ester; hydrobromide or hydrochloride salts of 2-(6-diethyl amino-3-ethyl imino-3H-xanthen-9-yl)-benzoic acid n-butyl diester; acetate salt of 2,7-dibromorhodamine B methyl ester; acetate salt of 2,7-dibromorhodamine B hexyl ester; hydrobromide or hydrochloride salts of 4,5-dibromorhodamine 6G; hydrobromide or hydrochloride salts of 2'-(6-dimethylamino-3-dimethylimino-3H-xanthen-9-yl) 4',5' dichloro-benzoic acid methyl ester; hydrobromide or hydrochloride salts of 4,5-dibromorhodamine 110 2-(2-methoxy ethoxy) ethyl ester and hydrobromide or hydrochloride salts of rhodamine B 3-bromopropyl ester; and photosensitive derivatives of these photosensitive compounds. In a preferred embodiment, a salt of 2-(4,5-dibromo-6-amino-3-imino-3H-xanthen-9-yl)-benzoic acid methyl ester (also known as 4,5-dibromorhodamine 123 methyl ester) is used, such as a hydrobromide or hydrochloride salt of 2-(4,5-dibromo-6-amino-3-imino-3H-xanthen-9-yl)-benzoic acid methyl ester, also referred to as TH9402, or 3,6-diamino-4,5-dibromo-9-(2-(methoxycarbonyl)phenyl) xanthylium chloride (CAS no. 174230-05-8).

Photoactivation of the above mentioned photosensitive rhodamines or rhodamine derivatives allow for selective killing of cells, because the photosensitive rhodamines or rhodamine derivatives are preferentially retained by certain cells such as tumor cells and activated cells. Other cells, such as non-tumor cells or non-activated cells, do not retain these photosensitive rhodamines or rhodamine derivatives and are therefore not affected.

The cell preparation in the medium comprising 5 micromolar or less of a photosensitive compound may be any preparation of cells. The cells are typically from an organ or a tissue of mammalian origin, preferably from a human being. In one embodiment, the cells are prepared from solid or soft tissue, such as liver or bone marrow. In another embodiment, the cells are prepared from non-solid tissue, such as blood, or in particular peripheral blood. In the context of the present invention, the term 'peripheral blood' means blood that is not: In the bone marrow or in the organs, i.e. the blood in the circulation.

The cell preparation in the medium comprising 5 micromolar or less of a photosensitive compound may comprise stem cells. In one embodiment, at least 60% of the cells, at least 70% of the cells, at least 80%, at least 90%, at least 95% or at least 99% of the cells in the cell preparation are stem cells. In the context of the present invention, the term 'stem cells' refers to undifferentiated cells which are omnipotent or pluripotent and which reside primarily in the bone marrow. In one embodiment, the cell preparation comprises 100% stem cells. The stem cells may be any kind of stem cells, in one embodiment, the preparation of stem cells comprises at least 60%, at least 70%, at least 80%, at least 90%, at least 95%, at least 99% hematopoietic stem cells. In another embodiment, the preparation of stem cells consists of hematopoietic stem cells.

The cell preparation in the medium comprising 5 micromolar or less of a photosensitive compound may comprise T-lymphocytes. In one embodiment, at least 10% of the cells, at least 20% of the cells, at least 30% of the cells, at least 40% or at least 50% of the cells, at least 60% of the cells, at least 70% of the cells, at least 80%, at least 90%, at least 95% or at least 99% of the cells in the cell preparation in the medium are T-lymphocytes. In one embodiment, the cell preparation comprises 100% T-lymphocytes. T-lymphocytes may be identified as cells which are both CD3+ and CD45+ and are also referred to as T-cells.

The cell preparation in the medium comprising 5 micromolar or less of a photosensitive compound is typically a cell preparation which one wishes to deplete from certain cells. In one embodiment, the cell preparation is to be depleted from tumor cells to ensure that transplantation of those treated cells will not cause tumor formation in the recipient.

In another embodiment, the cell preparation in the medium comprising 5 micromolar or less or a photosensitive compound is to be depleted from activated cells, in particular from activated leukocytes, more in particular from activated T-lymphocytes. In one embodiment, the cell preparation is a mixture of donor and recipient cells which needs to be depleted from recipient-activated donor cells, in particular from recipient-activated donor T-lymphocytes.

Activation of T-lymphocytes may be apparent from upregulation of certain surface markers, e.g. upregulation of the IL-2 receptor or subunits thereof, such as the IL-2 receptor alpha chain, also referred to as CD25, or from proliferation, i.e. dividing and multiplication. Proliferation may require proliferation factors such as for example interleukins, such as interleukin 2, or other growth factors and may be measured in a proliferation assay as described below.

Cells may be activated by any method known in the art. In one embodiment, the activation is effected by a mixed lymphocyte reaction (MLR). In the present context, a mixed lymphocyte reaction (MLR) refers to an ex vivo reaction wherein cell preparations from two individuals, at least one of them containing T-lymphocytes, are mixed to allow a proliferative response of the T-lymphocytes from one individual (the responder) to cells from another individual (stimulator). The MLR is preferably a one-way MLR, wherein the stimulator cells are treated to render them non-proliferative. A suitable way of rendering cells non-proliferative is by interfering with their DMA functionality, e.g. by gamma irradiation or by treating them with mitomycin C. Another suitable way of rendering the cells non-proliferative is to fixate the cells, e.g. by formaldehyde, or paraformaldehyde. The T-cells for MLR may be isolated or may be present in a preparation which also contains other types of cells. In one embodiment, the T-cells used in the MLR are present in a peripheral blood mononuclear cell (PBMC) fraction. The person skilled in the art knows how to prepare a PBMC fraction, e.g. by Ficoll®-gradient density centrifugation. T-cells used in the MLR are preferably not pre-activated, such as by anti-CD3 antibodies or interleukin-2. The use of pre-activated T-cells as responders may lead to unselective depletion of the cells during photodynamic treatment or exhaustion of the remaining T-cells post photodepletion which is not preferred. Use of pre-activated T-cells as stimulators in the MLR is also not preferred as these cells produce a cocktail of activating cytokines that causes unselective depletion.

In an MLR, cells are typically incubated for two to seven days, preferably four to five days. In one embodiment, donor and recipient cells are incubated for four days in a one-way MLR.

In one embodiment, the cell preparation in the medium comprising 5 micromolar or less of a photosensitive compound is an MLR mixture of donor and recipient cells obtained by a one-way MLR with lymphocytes from a healthy donor and non-proliferative lymphocytes from a recipient. In another embodiment, the cell preparation in the medium comprising 5 micromolar or less of a photosensitive compound is an MLR mixture of donor and recipient cells obtained by a one-way MLR with lymphocytes from a healthy donor and non-proliferative lymphocytes from a recipient, wherein some of the donor cells have become activated due to the donor and recipient being of non-identical HLA haplotype and the donor cells being activated by mismatched HLA antigens on the recipient cells.

The recipient may be a patient, e.g. a patient who has received or will receive a transplant from the donor. The transplant may be a tissue, organ or cells and may be solid or non-solid. In a preferred embodiment, the patient is a patient who has received or will receive stem cell transplantation, such as a blood cancer patient or a sickle cell anemia patient, or a granulomatosis patient, or a thalassemia patient or a recipient of a solid organ transplant. Donor and recipient may be of any species, preferably they are mammals. Preferably, the recipient is a human being, more preferably, both donor and recipient are human beings.

Cell preparations comprising donor and recipient cells may conveniently be used in a photodynamic process according to the invention for preventing graft-versus-host disease (GvHD) by specific elimination of donor cells which are activated by recipient cells. In the context of the present invention, the term graft-versus-host disease (GvHD) refers to a disease wherein, in the context of allograft transplantation, donor cells, in particular T-lymphocytes, attack recipient cells. GvHD may be acute or chronic, as classified by the symptoms and manifestation of the disease.

The cell preparation is incubated in a medium which comprises 5 micromolar or less of a photosensitive compound. In one embodiment, it comprises, 4 micromolar or less, 3 micromolar or less, 2 micromolar or less or 1 micromolar or less of a photosensitive compound. In one embodiment, the medium comprises from 0.1 to 5 micromolar of a photosensitive compound. In another embodiment, the medium comprises, from 0.5 to 5 micromolar of a photosensitive compound. In another embodiment, the medium comprises from 1 to 5 micromolar or 2 to 5 micromolar of a photosensitive compound. In yet another embodiment, the medium comprises from 0.5 to 4 micromolar, 1 to 4 micromolar or 2 to 4 micromolar of a photosensitive compound. In yet another embodiment, the medium comprises from 0.1 to 3 micromolar of a photosensitive compound. Suitable photosensitive compounds have been mentioned above. In one embodiment, the photosensitive compound is a rhodamine or rhodamine derivative as mentioned above.

The volume of the medium comprising 5 micromolar or less of a photosensitive compound must be sufficient to effectively color the cells with photosensitive compound and will be dependent on the weight of the patient. A suitable coloration volume is in general in the range of 300 to 1500 ml. For a 50 kilo patient, coloration may suitably be performed in 900 to 1100 ml. In one embodiment for a 50 kg patient coloration is performed in about 1000 ml. For a 100 kg patient, coloration may suitably be performed in 1300 to 1400 ml. In one embodiment, for a 100 kg patient it is performed in about 1375 ml.

The medium comprising 5 micromolar or less of a photosensitive compound may further comprise general cell culture constituents, such as plasma, serum or antibiotics. In one embodiment, the medium comprises donor plasma. A suitable medium composition which may be used is X-VIVO™ 15 medium without gentamicin and without phenol red (Lonza, USA) and 2.5% (v/v) heat-inactivated (HI) donor plasma.

Coloration may be performed at a temperature in the range of 20 degrees C. to 40 degrees C., preferably at a temperature in the range of 25 to 38 degrees C., more preferably at a temperature in the range of 36.5 to 37.5 degrees C. The $CO_2$ concentration is suitably about 5%, i.e. 4.5% to 5.5%. In one embodiment, coloration is performed at a temperature in the range of 36.5 to 37.5 degrees C. and with a $CO_2$ concentration of about 5%.

The cell preparation is incubated in medium comprising 5 micromolar or less of a photosensitive compound for as long as necessary to color, i.e., for the photosensitive compound to be taken up in, at least 90% of the cells in the preparation. Preferably, at least 95%, at least 97%, at least 98% or at least 99% of the cells in the preparation are colored. In a more preferred embodiment, all the cells in the preparation are colored. This typically takes 30 to 90 minutes. In one embodiment, at least 90% of the cells are colored in 30 to 90 minutes, preferably in 30 to 50 minutes, if $1\times10^6$ cells/ml is used. In another embodiment, at least 95% of the cells ere colored in 30 to 90 minutes, preferably in 30 to 50 minutes, if $1\times10^6$ cells/ml is used. In another embodiment, at least 96%, at least 97%, at least 98% or at least 99% of the cells are colored in 30 to 90 minutes, preferably in 30 to 50 minutes, if $1\times10^6$ cells/ml is used. In one embodiment, $1\times10^6$ cells/ml are incubated for 40 minutes with 5 micromolar or less of a photosensitive compound to color at least 99% of the cells and preferably all the cells in the preparation.

After coloration, the medium comprising 5 micromolar or less of a photosensitive compound is replaced by an extrusion medium, which results in selective staining of cells by extrusion of the photosensitive compound from non-activated cells. The extrusion medium is therefore substantially free of photosensitive compound and preferably comprises no photosensitive compound. Replacement is preferably achieved by using a separation method. Any separation method known in the art which is suitable to be used with cells, such as centrifugation, filtration and dialysis may be used. In one embodiment, the medium comprising 5 micromolar or less of a photosensitive compound is replaced by an extrusion medium by centrifuging the cell preparation after coloration to obtain a pellet and a supernatant. The pellet, containing the cells after coloration, is resuspended in extrusion medium which preferably comprises no photosensitive compound. By extrusion any residual, excess or unbound photosensitive compound, typically extracellular photosensitive compound, may be removed. The extrusion medium may further comprise general cell culture constituents, such as plasma, serum or antibiotics. In one embodiment, the extrusion medium comprises donor plasma. A suitable extrusion medium composition which may be used is X-VIVO™ 15 medium without gentamicin and without phenol red (Lonza, USA) with 10% (v/v) HI donor plasma.

Extrusion may be performed at a temperature in the range from 20 degrees C. to 40 degrees C., preferably at a temperature in the range from 25 to 38 degrees C., more preferably at a temperature in the range from 35.5 to 37.5 degrees C. The $CO_2$ concentration is suitably about 5%, i.e. 4.5% to 5.5%. In one embodiment, extrusion is performed at a temperature in the range of 36.5 to 37.5 degrees C. and with a $CO_2$ concentration of about 5%.

According to the method of the invention, extrusion may be performed in convenient volumes, which are easy to handle and which are smaller than in state of the art methods. Therefore, extrusion volumes are in the range from 330 to 600 ml. In one embodiment, the extrusion volume is maximally 500 ml, e.g. 330-500 ml. Preferably, the extrusion volume is maximally 450 ml, e.g. 330-400 ml. Such volumes facilitate standardization because all cells can be treated in one experiment, at the same time and under the same conditions, instead of having to perform several rounds of experiments under possibly slightly different conditions. The cell concentration in the extrusion phase is typically higher than the cell concentration in the coloration phase. In one embodiment, the ratio of the cell concentration in the coloration phase:the cell concentration in extrusion equals at least 1:2. In another embodiment, the ratio of the cell concentration in the coloration phase:the cell concentration in extrusion equals at least 1:3. A higher cell concentration in the extrusion phase than in the coloration phase allows for important medium reduction, processing more cells with equal devices and facilitates scalability.

The cell preparation is incubated in extrusion medium for as long as necessary to remove any residual, excess or unbound, typically extracellular, photosensitive compound. This typically takes from 60 to 100 minutes. In one embodiment, at least $1\times10^6$ cells/ml are incubated in a total volume of maximally 600 ml, e.g. 330-600 ml, or maximally 500 ml, preferably maximally 400 ml, e.g. 330-400 ml, extrusion medium for 60 to 90 minutes, preferably 80 to 90 minutes, with effective extrusion of any residual, excess or unbound, typically extracellular, photosensitive compound. In another embodiment, at least $2\times10^6$ cells/ml are incubated in a total volume of maximally 500 ml, e.g. 330-500 ml, preferably 330-400 ml extrusion medium for 60 to 90 minutes, preferably 80 to 90 minutes, with effective extrusion of any residual, excess or unbound, typically extracellular, photosensitive compound. In yet another embodiment, at least $3\times10^6$ cells/ml are incubated in a total volume of maximally 600 ml or maximally 500 ml, e.g. 330-500 ml, preferably in maximally 400 ml extrusion medium for 60 to 90 minutes, preferably 80 to 90 minutes, with effective extrusion of any residual, excess or unbound, typically extracellular, photosensitive compound. In one embodiment, $2\times10^6$ cells/ml are extruded in maximally 400 ml e.g. 330-400 ml, extrusion medium after coloration with 5 micromolar photosensitive compound. In another embodiment, $3\times10^6$ cells/ml are extruded in maximally 400 ml e.g. 330-400 ml, extrusion medium after coloration with 5 micromolar photosensitive compound. Extrusion is effective if more dye is extruded from the non-activated cells than from the activated cells, resulting in a distinct dye concentration in activated versus non-activated cells.

After extrusion, the cells in extrusion medium are illuminated to selectively kill the cells which have retained the photosensitive compound.

Light for photodynamic treatment is preferably delivered by an illumination device which provides uniform light delivery across a large surface. The cells are preferably positioned in such a way that there is optimal exposure of the cells to the light from the illumination device. Therefore, cells are preferably presented in or as a thin layer. The thin layer of cells is preferably 20 mm or less, more preferably 15 mm or less or 10 mm or less, most preferably 5 mm or less, 4.5 mm or less, 3 mm or less, 3.5 mm or less or 3.0 mm or less. In one embodiment, the thin layer of cells is between 1.0 mm and 20 mm, between 1.0 mm and 15 mm, between 1.0 mm and 10 mm or between 10 mm and 5 mm. In another embodiment, the thin layer of cells is between 1.0 mm and 4.5 mm, between 1.0 mm and 4.0 mm, between 1.0 mm and 3.5 mm, between 1 mm and 3 mm, between 1 mm and 2.5 mm or between 1 and 2 mm. In yet another embodiment, the thin layer of cells is between 2.0 mm and 4.5 mm, between 2.0 mm and 4.0 mm, between 2.0 mm and 3.5 mm. In yet another embodiment, the thin layer of cells is between 2.5 mm and 4.5 mm, between 2.5 mm and 4.0 mm, between 2.5 mm and 3.5 mm or between 2.5 mm and 3 mm.

The skilled person will understand that uniform light delivery and optimal exposure of cells to light may be achieved in several ways. In one embodiment, this is achieved by using an illumination device which scans the cells while they are in a thin layer. In another embodiment, this is achieved by using a scanning illumination device which moves in two opposite directions and which illuminates the cells while they are in a thin layer. An example of a suitable device is a scanning illumination device which can move in two opposite directions and which can illuminate the cells comprising the photosensitive compound from below while the cells are in a thin layer. The thin layer may e.g. be obtained by positioning the cells in a flat position.

In one embodiment, the area which is covered by the scanning device is preferably 1200-1800 square cm, e.g. about 40×40 cm or 36×34 cm. A suitable illumination device is described in WO98/03224 or is the Theralux™ illumination device (Kiadias Pharma, Canada). In one embodiment, the thin layer of cells comprising the photosensitive compound is gently shaking, in another embodiment, the thin layer of cells comprising the photosensitive compound is stationary or statically, i.e. not moving.

Photodynamic treatment is stopped when an energy dose in the range from 4 to 5 $J/cm^2$ is delivered to the cells in the extrusion medium. It will depend on the light source how long it will take before 4 to 5 $J/cm^2$ is delivered to the cells in the extrusion medium. In one embodiment, light exposure is continued for 35 to 45 minutes in order to deliver 5 $J/cm^2$ to the cell preparation in extrusion medium. After light exposure, cells are collected and centrifuged to remove the extrusion medium.

The light used in the photodynamic process according to the invention is electromagnetic radiation which has a wavelength of a visible wavelength. The electromagnetic radiation has a wavelength, in the range from 400 to 700 nm, preferably in the green spectrum, i.e. in the range from 500 to 580 nm, more preferably in the range from 510 to 550 nm, most preferably in the range from 510 to 520 nm. In one embodiment, electromagnetic radiation with a wavelength in the range from 512 to 514 nm is used for activating the photosensitive compound to generate a cytotoxic product, such as e.g. cytotoxic singlet oxygen.

The exposure to light may be in any suitable way, and may be in vivo or ex vivo. In a preferred embodiment the exposure to light is ex vivo.

The total number of cells which may be treated in at the same time and under the same conditions in the photodynamic treatment process according to the invention, and in particular during extrusion and illumination, is 150 million cells to $1.8 \times 10^9$ cells. In one embodiment, at least $1 \times 10^8$ cells or at least $1 \times 10^9$, are treated at the same time and under the same conditions. In another embodiment, $1.2 \times 10^9$ cells are treated at the same time and under the same conditions.

This is much more than would be possible with the state of the art process. These cells may be present in a concentration of at least $1 \times 10^6$ cells/ml or of at least $2 \times 10^6$ cells/ml. In one embodiment, the cells are present in a concentration of at least $3 \times 10^6$ cells/ml. As a result, the volumes involved are easy to handle.

Photodynamic dynamic treatment is effective if at least 80% of the cells which retain the photosensitive compound are killed. In one embodiment, at least 85% of the cells which retain the photosensitive compound are killed. In yet another embodiment, at least 90%, at least 95%, at least 97%, at least 98% or at least 99% of the cells which retained the photosensitive compound is killed. Preferably, all the cells which retained the photosensitive compound are killed. The cell product obtained using the photodynamic process according to the invention is improved with regard to relevant characteristics in comparison to a cell product obtainable by a reference process using 10 micromolar photosensitive compound.

Therefore, in another aspect, the present invention relates to a cell product obtained by using the photodynamic process according to the present invention.

In one embodiment, the cell product is a population of cells depleted of cancer cells, in particular a population of cells depleted of cancer cells, whereby the population of cells is to be transplanted into a recipient.

In another embodiment, the cell product is a host-recipient lymphocyte preparation depleted of recipient responsive T-lymphocytes. Such a cell product may for example be obtained in the context of allografting, if the starting cell preparation is an MLR mixture of donor and recipient cells obtained by a one-way MLR with lymphocytes from a healthy donor and non-proliferative lymphocytes from a recipient, wherein some of the donor cells have become activated due to the donor and recipient being of non-identical HLA haplotype and the donor cells being activated by mismatched HLA antigens on the recipient cells. Such a cell product may also be referred to as a T-cell enriched donor lymphocyte preparation selectively depleted of alloreactive T-cells. Such a cell product is improved with regard to one or more of WBC recovery, WBC viability, viable T-cell content, 2-day T-cells survival and proliferation after freezing and thawing in comparison to a cell preparation prepared by a reference process using 10 micromolar of a photosensitive compound. In one embodiment, the lymphocyte preparation depleted of recipient responsive T-lymphocytes prepared by using the photodynamic process according to the invention is improved with regard to WBC recovery, WBC viability, viable T-cell content, 2-day T-cells survival and proliferation after freezing and thawing in comparison to a cell preparation prepared by a reference process using 10 micromolar of a photosensitive compound. Suitable photosensitive compounds include rhodamines and rhodamine derivatives, in particular dibromorhodamine derivatives, such as salts of 2-(4,5-dibromo-6-amino-3-imino-3H-xanthen-9-yl)-benzoic acid methyl ester (also known as 4,5-dibromorhodamine 123 methyl ester) and also referred to as TH9402. Other suitable photosensitive compounds are as mentioned above for the photodynamic process.

An improved WBC recovery is reflected in a higher percentage of WBCs being recovered, whereby the WBC concentration before freezing is taken as 100%.

An improved WBC viability is reflected in a higher viable WBC concentration in cells/ml of the cell product.

An improved viable T-cell content is reflected in a higher viable T-lymphocytes concentration in cells/ml of the cell product.

An improved 2-day T-cell survival is reflected in a higher percentage of T-lymphocytes being alive in the cell product 2 days after thawing, whereby the viable T-cell concentration in cells/ml after thawing is taken as 100%.

An improved proliferation profile is reflected in a similar or lower proliferation to autologous cells combined with a similar or lower proliferation to recipient cells or a similar or higher proliferation to $3^{rd}$ party cells. In one embodiment, the improved proliferation profile is reflected in a similar proliferation to autologous cells in combination with a similar proliferation to recipient cells and a higher proliferation to $3^{rd}$ party cells. In another embodiment, the improved proliferation profile is reflected in both a lower proliferation to autologous cells and a lower proliferation to recipient cells and a higher proliferation to $3^{rd}$ party cells.

This improved cell product which is obtainable by the process of the present invention may be used in a method for preventing or treating cancer or in a method for preventing or treating graft-versus-host disease. Preferably it is formulated for pharmaceutical use. It may be formulated in any suitable form known by the skilled person. In one embodiment it is formulated as a liquid, preferably as a liquid for single dose administration by infusion.

The proliferation profile of the cell product obtained may be determined in a proliferation assay. Any suitable proliferation assay may be used. In one embodiment, a proliferation assay is used using cells loaded with carboxyfluorescein diacetate succinimidyl ester (CFSE) and wherein cell cultures were initiated by addition of different proliferation-inducing stimuli for five days in the presence of 1 IU/ml human interleukin-2 in X-VIVO™ 15 medium with 10% (v/v) pooled human heat-inactivated plasma. The proliferation (i.e. dilution of CFSE) of the cells may be analyzed using Modfit LT™ software returning a proliferation index (PI) which reflects the increase in cell number over the course of the assay. A PI of 1.0 represents no proliferation. Suitable proliferation inducing stimuli depend on the cells to be depleted, but may include:
1. irradiated autologous donor cells, to determine baseline proliferation by addition of cells that may provide a 'feeder effect'. Feeder cells release nutrients and provide for matrix support;
2. irradiated recipient cells, to determine the (retained) reactivity against the recipient, which reactivity is preferably absent or close to the baseline;
3. irradiated 3rd party cells, to determine the (retained) reactivity against unrelated HLA-antigens, which reactivity is preferably retained and in any way at least twice the retained reactivity against the recipient, as mentioned above under 2.

$$\frac{PI(3^{rd} \text{ party}) - 1}{PI(\text{recipient}) - 1} \geq 2$$

In one embodiment, this ratio is at least three or at least four, in another embodiment, it is between four and five.

Viable WBC concentration may be determined by any method known to the skilled person, e.g. by using a haemocytometer and a Trypan blue staining. The person skilled in the art knows how to perform a Trypan blue staining, e.g. by applying an appropriately diluted cell preparation mixed with a 0.4% Trypan blue solution for 3-30 minutes on to a haemocytometer and microscopically counting the number of viable and non-viable cells by determining the number of Trypan blue-negative and Trypan blue-positive cells, respectively. Alternatively, viable WBC concentration may be determined by flow cytometry, automated cell counters or others following the manufacturer's instruction.

The concentration of viable T-cells in the cell product may be determined by any method known to the skilled person. In one embodiment it is calculated by determining the proportion of viable T-cells in the WBC fraction. This may be calculated by initiating triplicate cultures at a viable WBC concentration of $3 \times 10^6$/ml in plasma supplemented with 1 IU/ml recombinant human interleukin-2. Twenty-four hours after initiation of the cultures, the WBC concentration is determined using a hematology analyzer, for example by using an ABX® Micros ES60 (Horiba ltd., Japan) or any other hematology analyzer, and the percentage of viable T-cells is determined by staining the cells in the fraction with a suitable antibody panel. A suitable antibody panel may include anti-CD3, anti-CD45 and 7-amino-actinomycin D (7AAD) for the detection and determination of T-cells, white blood cells and for the exclusion of non-viable cells, respectively. The percentage of viable T-cells may be determined by analyzing the percentage of CD3 positive best 7AAD negative cells within the CD45 positive cells. Multiplying this percentage of T-cells by the WBC concentration determined by using the hematology analyzer will yield the concentration of viable T-cells in cells/ml.

In another aspect, the present invention relates to the use of the photodynamic process according to the invention in a method of treatment. All the embodiments mentioned above for the photodynamic process are also applicable to this aspect.

In one embodiment, the present invention relates to the use of the photodynamic process according to the invention in a method for reducing or preventing graft-versus-host disease, in particular graft-versus-host disease associated with allogeneic stem cell transplantation, by specific elimination of donor cells which are activated by recipient cells. In one embodiment, the photodynamic process according to the invention is used in a method for reducing or preventing graft-versus-host disease comprising the ex vivo steps of (i) activating lymphocytes from a donor by mixing donor cells from a healthy donor with non-proliferative recipient cells from a patient for a period of time sufficient to activate the donor cells, (ii) selectively killing the activated lymphocytes of step (i) using photodynamic therapy using 5 micromolar or less of a photosensitive compound and (iii) infusing the mixture obtained in (ii) in the patient. The lymphocytes are preferably T-lymphocytes. Such infusion is typically given to the patient 4-5 weeks after the stem cell transplantation in order to quickly provide the patient with mature T-lymphocytes, which otherwise would have taken several months to form.

In another embodiment, the present invention relates to the use of the photodynamic process according to the invention in a method for killing cancer cells within a population of cells which also comprises non-cancer cells, in particular within a population of cells which is to be transplanted into a recipient. In one embodiment, the photodynamic process according to the invention is used to kill cancer cells in bone marrow, in particular in bone marrow for autologous stem cell transplantation. In one embodiment, the photodynamic process according to the invention is used in a method for treating a cancer patient comprising the ex vivo steps of (i) harvesting the patient's bone marrow; (ii) selectively killing the cancer cells in the patient's bone marrow using photodynamic therapy using 5 micromolar or less of a photosensitive compound and (iii) performing autologous stem cell transplantation using the treated bone marrow of (ii).

In another aspect, the present invention relates to a pharmaceutical composition comprising the cell product according to the invention and a pharmaceutical carrier. In one embodiment, the pharmaceutical composition is used in a method for preventing or treating cancer. In another embodiment, the pharmaceutical composition is used in a method for preventing or treating acute graft-versus-host disease. In yet another embodiment, the pharmaceutical composition is a pharmaceutical composition for preventing or treating chronic graft-versus host disease.

In another aspect, the present invention relates to a method for the ex vivo treatment of cells, wherein the method comprises the ex vivo steps of activating lymphocytes from a donor by (i) mixing lymphocytes comprising donor cells from a healthy donor with non-proliferative recipient cells from a patient for a period of time sufficient to activate the donor cells, (ii) selectively killing the lymphocytes activated in step (i) using photodynamic therapy using 5 micromolar or less of a photosensitive compound and (iii) infusing the mixture obtained in (ii) in a patient. Preferably, the selective killing in (ii) comprises incubation of the cells in an extrusion medium which results in selective staining of the activated donor lymphocytes. The lymphocytes are preferably T-lymphocytes.

In another aspect, the present invention relates to a method for the ex vivo treatment of cells, wherein the method comprises the ex vivo steps of (i) incubating a cell preparation in a medium comprising 5 micromolar or less of a photosensitive compound; (ii) replacing the medium of (i) with an extrusion medium to remove the photosensitive compound and (iii) illuminating the cell preparation in the extrusion medium to selectively kill those cells which retained the photosensitive compound.

In another aspect, the present invention relates to a kit which is suitable for use in a process or method according to the invention, wherein the kit comprises (i) a photosensitive compound for use in a concentration of 5 micromolar or less for ex vivo treatment of cells by illumination and (ii) extrusion medium for removal of photosensitive compound leading to selective staining of cells. In one embodiment, the kit further comprises an illumination device. Suitable extrusion media nave been described above in other aspects of the invention and are used for removal of any residual, excess or unbound, typically extracellular, photosensitive compound leading to selective staining of cells. Preferably, the extrusion medium is substantially free of photosensitive compound. More preferably, the extrusion medium comprises no photosensitive compound. In one embodiment, the photosensitive compound is a photosensitive rhodamine or rhodamine derivative. Suitable rhodamines and rhodamine derivatives have been mentioned above and include in particular dibromorhodamine derivatives, such as salts of 2-(4,5-dibromo-6-amino-3-imino-3H-xanthen-9-yl)-benzoic acid methyl ester (also known as 4,5-dibromorhodamine 123 methyl ester) and also referred to as TH9402.

All the embodiments mentioned above for one aspect of the invention are also applicable to the other aspects of the invention.

EXAMPLES

Materials & Methods

Mixed Lymphocyte Reaction (MLR)

For a mixed lymphocyte reaction (MLR), mononuclear cells from a donor and from a recipient were isolated by Ficoll® (GE Healthcare, United Kingdom)-gradient density centrifugation according to the manufacturer's instructions. Next, the mononuclear cells from the healthy donor were mixed with γ-irradiated mononuclear cells from the recipient. This MLR mixture was prepared in bulk containing $1\times10^6$ viable donor white blood cells/ml and $1\times10^6$ viable recipient white blood cells/ml in MLR medium (X-VIVO™ 15 medium without gentamicin and without phenol red (Lonza, USA) plus 2% heat-inactivated (HI) donor plasma) containing 50 IU/ml exogenous IL-2 (Proleukin®, Novartis, Germany). The MLR cells were dispensed in TC-175 culture flasks (Sarstedt, Germany), each receiving 70 ml of MLR suspension. The flasks were incubated at 37° C., 5% $CO_2$ for four days, in a static position.

Coloration

After four days, the post-MLR cells were centrifuged. The resulting pellets were pooled and resuspended in X-VIVO™ 15 medium without gentamicin and without phenol red (Lonza, USA) and 2.5% HI donor plasma (coloration medium). The viable white blood cell (WBC) concentration of this cell suspension was determined by a hematology analyzer (Horiba Ltd. Japan,) together with a manual Trypan Slue count (0.4% Trypan blue; Sigma Aldrich, United Kingdom; mixing cells with Trypan blue for minimally 3 minutes, maximally 30 minutes). The post-MLR cell mixture was diluted in coloration medium to a viable WBC concentration of $1.11\times10^6$ cells/ml. Next, this diluted MLR mixture with a viable WBC concentration of $1.11\times10^6$ cells/ml was mixed in a 1:10 ratio with the dibromorhodamine derivative TH9402 (Kiadis Pharma, the Netherlands), which is 2-(4,5-dibromo-6-amino-3-imino-3H-xanthen-9-yl)-benzoic acid methyl ester, in coloration medium, yielding a coloration mixture containing X-VIVO™ 15 medium without gentamicin and without phenol red (Lonza, USA), 2.5% HI donor plasma, $1.0\times10^6$ viable WBCs/ml and TH9402 in a desired concentration. This coloration mixture was statically incubated in TC-175 (Sarstedt, Germany) flasks at 37° C., 5% $CO_2$. After 40 minutes of coloration, cells were harvested and centrifuged to remove the TH9402-containing medium.

Extrusion

Next, the cell pellet was resuspended in extrusion medium (X-VIVO™ 15 medium without gentamicin, without phenol red (Lonza, USA) and 10% HI donor plasma) to a desired final viable WBC concentration based on the cell count that was performed on the pooled post-MLR cells. The cells in extrusion medium were transferred to TC-175 flasks (Becton Dickinson, USA), 10 or 50 ml each, and statically incubated in a flat position at 37° C., 5% $CO_2$. After 90 minutes of extrusion, the Basks containing the cells in extrusion medium were immediately subjected to photodynamic therapy.

Photodynamic Treatment (POT)

For photodynamic treatment, the flasks containing the cells in extrusion medium were placed on an illumination device for photodynamic treatment (Theralux™ device Kiadis Pharma, the Netherlands) in a flat position, side-by-side, and exposed to light with a wavelength of 514 nm (green spectrum) while gently shaking. Treatment was stopped when an energy dose of 5 J/cm² was delivered by the device, which took 35 minutes. After light exposure, cells were collected and centrifuged to remove the extrusion medium.

Cell Wash After PDT

Next, the cell pellets were pooled in wash medium (0.9% NaCl (Baxter, United Kingdom), 10% donor plasma) and the percentage of viable T-cells in the total WBC population was determined by flow cytometry (FACSVerse™, Becton Dickinson, USA). After a second wash, the WBC concentration was determined by a hematology analyzer (ABX® Micros ES60, Horiba Ltd. Japan). From the two measurements (percentage viable T-cells and WBC concentration) the viable T-cell concentration in this fraction was calculated.

Storage

A volume of viable T-cells corresponding to $7.5\times10^6$/ml from the post-PDT cell fraction was centrifuged and the cell pellet was resuspended in freeze medium A (saline with 20% donor HI plasma). Next, an equal volume of pre-cooled (2-8° C.) DMSO-containing medium (freeze medium B: saline with 40% donor HI plasma and 20% DMSO) was added to freeze medium A cell suspension and the mixture was dispensed over sample vials. The sample vials were frozen immediately in a controlled rate freezer, using a standard PBMC freezing program. The samples were stored in the liquid N2 vapor phase until further experiments, such as a proliferation profile, were performed Determination of the Percentage of Viable T-cells Within WBC Fraction The proportion of viable T-cells in the WBC fraction was determined by initiating triplicate cultures at a viable WBC concentration of $3\times10^6$/ml in plasma supplemented with 1 IU/ml recombinant human interleukin-2. Viable WBC concentration was determined using a hemacytometer (Labor Optik, United Kingdom). Twenty-four hours or 48 hours after initiation of the cultures, the WBC concentration was determined using a hematology analyzer (ABX® Micros ES60, Horiba Ltd., Japan), and the percentage of viable T-cells was determined by staining the cells in the fraction with an antibody panel which included anti-CD3 (V500-conjugated, mouse IgG1, clone UCHT1, Becton Dickinson, USA), CD45 (V450-conjugated mouse IgG1, clone HI30, Becton Dickinson, USA and 7AAD (Becton Dickinson, USA) for the detection and determination of T-cells, white blood cells and viability, respectively. The percentage of viable T-cells was determined by analyzing the percentage of CD3 positive but 7AAD negative cells within the CD45 positive cells. Multiplying this percentage of T-cells by the WBC concentration determined by using the hematology analyzer yielded the concentration of viable T-cells within the WBC fraction.

Determination of Percentage T-cell Survival

The viable T-cell concentration after thawing of the samples was set as 100%. The viable T-cell concentration measured after forty-eight hours of culture was divided by the viable T-cell concentration directly after thaw and multiplied by 100%, leading to a T-cell survival (%).

Determination of Viable WBC Concentration

The viable WBC concentration was determined before freezing and after thaw using a haemocytometer (Labor Optik, United Kingdom) or a using a hematology analyzer (ABX® Micros ES60, Horiba Ltd., Japan) according to the respective manufacturer's instruction.

Calculation of Viable T-cell Concentration in the Cell Product

The viable T-cell concentration of samples was calculated by multiplying the percentage of viable T-cells in the WBC fraction by the viable WBC concentration.

Determination of WBC Recovery

The WBC concentration after thawing of the samples was divided by the WBC concentration before freezing of the samples and multiplied by 100%, leading to a WBC recovery (%).

Comparative Example 1

A mixed lymphocyte reaction was carried out with $1\times10^6$ viable donor white blood cells/ml and $1\times10^6$ viable recipient white blood cells/ml in MLR medium. The MLR cells were dispensed in TC-175 culture flasks (Sarstedt, Germany), each receiving 70 ml of MLR suspension. The flasks were incubated at 37° C., 5% $CO_2$ for four days, in a static position and subsequently, the contents from the TC-175 flask were collected and centrifuged. The pellet was resuspended to a viable WBC concentration of $1.11\times10^6$ cells/ml in coloration medium and mixed with 100 μM TH9402 in coloration medium, leading to a coloration mixture containing 10 μM TH9402 and $1.0\times10^6$ viable WBCs/ml. This coloration mixture was statically incubated in TC-175 (Sarstedt, Germany) flasks at 37° C., 5% $CO_2$. After 40 minutes of coloration, cells were harvested and centrifuged to remove the TH9402-containing medium. Next, the cell pellet was resuspended in extrusion medium to a final viable WBC concentration of $1\times10^6$/ml in a total volume of 1200 ml (10 ml per flask), in order to treat all $1.2\times10^9$ cells, 120 flasks were required. Since the illumination device used (Theralux™, Kiadis Pharma, the Netherlands) could hold ten flasks containing 10 ml of cells each, three devices and four rounds of treatment were required to treat all the cells. After 90 minutes of extrusion the flasks containing the cells in extrusion medium were immediately subjected to photodynamic therapy at 514 nm using a Theralux™ PDT device (Kiadis Pharma, the Netherlands) in a flat position. A total energy of 5 J/cm2 was delivered in 35 minutes. After light exposure, cells were collected and centrifuged to remove the extrusion medium. After a first wash, the percentage of viable T-cells in the total WBC population was determined by flow cytometry as described above on a FACSVerse™ (Becton Dickinson, USA). After a second wash the concentration of WBC was determined using a hematology analyzer (ABX® Micros ES60, Horiba Ltd., japan) and the viable T-cell concentration in the product was calculated. The results are summarized in Table 1.

Comparative Example 2

In order to reduce the volume to be handled in the extrusion phase, a mixed lymphocyte reaction with $1\times10^6$ viable donor white blood cells/ml and $1\times10^6$ viable recipient white blood cells/ml was carried out in MLR medium as described in Example 1. This was followed by a coloration step as described in Example 1. However, the cell pellet after coloration was resuspended in extrusion medium to a final viable WBC concentration which was three times as concentrated as in Example 1, i.e. $3\times10^6$/ml, and larger flasks were used (50 ml per flask). The total volume to be treated was 400 ml. Now, in order to treat all $1.2\times10^9$ cells, only eight flasks were required. After 90 minutes of extrusion, cells were treated as in Example 1 and the concentration of WBC was determined and the viable T-cell concentration in the product was calculated. To be of value for clinical purposes, it was important that the concentration of viable T-cell in the product would be similar to example 1. However, the results, which are summarized in Table 1, show that reducing the volume influenced the quality of the product. The concentration of viable T-cells in the product was decreased significantly, which makes it unfit for final product dosage formulation.

Example 3

In an experiment under conditions according to the invention, a mixed lymphocyte reaction with $1\times10^6$ viable donor white blood cells/ml and $1\times10^6$ viable recipient white blood cells/ml was carried out in MLR medium as described in Example 1. After four days at 37° C., 5% $CO_2$, the contents from the TC-175 flask were collected and centrifuged. The pellet was resuspended to a viable WBC concentration of $1.11 \times 10^6$ cells/ml in coloration medium and mixed with 50 μM TH9402 in coloration medium, instead of 100 μM, leading to a coloration mixture containing 5 μM TH9402 and $1.0 \times 10^6$ viable WBCs/ml. This coloration mixture was statically incubated in TC-175 (Sarstedt, Germany) flasks at 37° C., 5% $CO_2$. After 40 minutes of coloration, the cells were harvested and centrifuged to remove the TH9402-containing medium. Next, the cell pellet was resuspended in extrusion medium to a final viable WBC concentration of $3 \times 10^6$/ml in a total volume of 400 ml (50 ml per flask). In order to treat all $1.2 \times 10^9$ cells, only eight flasks were required. After 90 minutes of extrusion, cells were treated as described in example 1. The concentration of WBC was determined and the viable T-cell concentration in the product was calculated.

TABLE 1

Fraction and concentration of viable T-cells obtained in experimental conditions.

| Example | μM TH9402 | Cell concentration during extrusion | % viable T-cells/ WBC Avg | Sd | Concentration viable T-cells ($\times 10^6$/ml product) Avg | Sd |
|---|---|---|---|---|---|---|
| Ex. 1 | 10 | $1 \times 10^6$/ml | 51.5 | 10.2 | 0.34 | 0.10 |
| Ex. 2 | 10 | $3 \times 10^6$/ml | 22.0 | 13.2 | 0.11 | 0.04 |
| Ex. 3 | 5 | $3 \times 10^6$/ml | 50.7 | 10.3 | 0.35 | 0.06 |

The characteristics of the cell product obtained by the process according to the invention, such as the viable T-cell concentration, are presented in Table 1. Surprisingly, using less photoactive compound allows for more cells to be treated at the same time and under the same conditions. It allows for volumes to be reduced, while maintaining a concentration of viable T-cells which is comparable to the reference product obtained in Example 1 and which is suitable for final product dosage formulation. ($1 \times 10^6$/ml; 10 μM). This means that the use of less photosensitive compound allows for the use of smaller volumes, but gives comparable results. The cell product was stored frozen until proliferation profile measurements were performed.

Example 4

Proliferation Profile of the Product Obtained

In this Example, the proliferative characteristics of the product obtained by the photodynamic process according to the invention were compared to the proliferative characteristics of the reference product obtained in Example 1. The cell product prepared in Examples 3 was thawed and the viable WBC concentration was determined using a haemocytometer and Trypan blue staining. Then, the cell suspension was loaded with 1 μM carboxyfluorescein diacetate succinimidyl ester (CFSE, Molecular Probes, USA) at a fixed WBC concentration of $2 \times 10^6$/ml. The cell product prepared in comparative Example 1 was used as a reference.

Cell cultures were initiated by addition of three different proliferation-inducing stimuli for 5 days in the presence of 1 IU/ml human interleukin-2 in X-VIVO™ 15 medium with 10% pooled human heat-inactivated plasma. The three proliferation inducing stimuli were:

1. irradiated autologous donor cells, to determine baseline proliferation by addition of cells that may provide a 'feeder effect'
2. irradiated recipient cells, to determine the (retained) reactivity against the recipient, that is associated with GvHD
3. irradiated 3rd party cells, to determine the (retained) reactivity against unrelated HLA-antigens.

The proliferation (i.e. dilution of CFSE) of the cells was analyzed using Modfit LT™ software returning a proliferation index (PI) which reflects the increase in cell number over the course of the assay; a PI of 1.0 represents no proliferation. The original process was known to result in a product that exhibited a proliferation index (PI) towards recipient cells with which the donor cells were stimulated in the manufacturing process that was close to baseline conditions (i.e. stimulation with autologous donor cells). Yet, the PI towards $3^{rd}$ party cells should be clearly detectable. Results are shown in Table 2.

As shown in Table 2, the photodynamic process according to the invention resulted in a product having an improved post-thaw proliferation index towards third party cells in comparison with the reference product obtained in Example 1.

TABLE 2

Proliferation Indexes obtained in experimental conditions.

| Cell concentration | μM TH9402 | PI baseline Avg | Sd | PI Recipient Avg | Sd | PI $3^{rd}$ Party Avg | Sd |
|---|---|---|---|---|---|---|---|
| $1 \times 10^6$/ml | 10 | 1.06 | .04 | 1.06 | .03 | 1.20 | .08 |
| $3 \times 10^6$/ml | 5 | 1.06 | .05 | 1.09 | .06 | 1.31 | .01 |

Example 5

Product Characteristics after Freezing and Thawing

In a separate set of experiments, the characteristics of a cell product according to the invention were compared to a reference product obtained using a process according to Example 1 with respect to post-thaw WBC recovery, WBC viability, viable T-cell content, 2-day T-cells survival and proliferation. Samples from both processes were frozen and after thaw analyzed for WBC recovery, WBC viability, viable T-cell content, 2-day T-cells survival and proliferation. The average of three experiments with the same source material is shown in Table 3.

TABLE 3

Post-thaw cell product characteristics
(Average of three experiments ± Standard deviation).

| | Reference product | Invention cell product |
|---|---|---|
| WBC recovery (%) | 43.0 ± 4.0 | 53.7 ± 2.1 |
| WBC viability (cells/ml) | 54.2 ± 13.5 | 57.8 ± 14.4 |
| Viable T-cell content (%) | 46.9 ± 11.1 | 50.5 ± 10.4 |
| 2-day T-cell survival (%) | 43.3 ± 12.7 | 52.8 ± 11.4 |
| Proliferation autologous (PI) | 1.07 ± 0.03 | 1.05 ± 0.01 |
| Proliferation recipient (PI) | 1.11 ± 0.05 | 1.09 ± 0.03 |
| Proliferation $3^{rd}$ party (PI) | 1.41 ± 0.11 | 1.50 ± 0.16 |

Surprisingly, the process according to the invention yielded a product which was improved in comparison to the reference product. More WBCs were recovered after thaw with a higher viability and a higher viable T-cell content, indicating that the post-thaw dose of the product according to the invention contains a higher concentration of active component. Additionally, the 2-day T-cell survival was higher, indicating that the active component in the product according to the invention will persist longer in vivo. Finally, the proliferation characteristics of the product after the invention show a superior pattern: lower proliferation to autologous cells, lower proliferation to recipient cells and a higher proliferation to 3rd party cells. Thus, the process after the invention yields a product that is better depleted of the unwanted recipient-reactive cells, but has retained more reactivity against unrelated $3^{rd}$ party antigens.

In conclusion, the process after the invention yields a more viable product with longer persisting cells that have superior proliferating capacities.

The invention claimed is:

1. A method for ex vivo photodynamic treatment of cells, comprising the steps of:
    incubating a cell preparation in a first medium comprising 5 µM of a photosensitive compound, wherein the cell preparation in the first medium has a first cell concentration, wherein a population of cells retains the photosensitive compound, wherein the photosensitive compound is a salt of 2-(4, 5-dibromo-6-amino-3-imino-3H-xanthen-9-yl)-benzoic acid methyl ester;
    replacing the first medium with an extrusion medium to remove the photosensitive compound, wherein the cell preparation in the extrusion medium has a second cell concentration, and wherein the ratio of the first cell concentration to the second cell concentration is 1:3; and
    illuminating the cell preparation in the extrusion medium to selectively kill the population of cells retaining the photosensitive compound, thereby creating an illuminated cell preparation.

2. The method of claim 1, wherein the salt of 2-(4, 5-dibromo-6-amino-3-imino-3H-xanthen-9-yl)-benzoic acid methyl ester is a hydrobromide or hydrochloride salt.

3. The method of claim 1, wherein the cell preparation in the medium comprising 5 µM of a photosensitive compound was first subjected to a mixed lymphocyte reaction.

4. The method of claim 1, wherein the cell preparation in the medium comprising 5 µM of a photosensitive compound comprises T-lymphocytes from a first person and non-proliferative T-lymphocytes from a second person.

5. The method of claim 4, wherein the first person is a donor and the second person is a recipient.

6. The method of claim 1, wherein the population of cells that retains the photosensitive compound are recipient-activated donor cells.

7. The method of claim 6, wherein the recipient-activated donor cells are alloreactive T-lymphocytes.

8. The method of claim 5, further comprising the step of infusing the illuminated cell preparation into the second person.

9. The method of claim 5, wherein the second person has cancer.

10. The method of claim 5, wherein the second person is a transplant patient.

11. The method of claim 1, the first medium is replaced with the extrusion medium using a separation method.

12. The method of claim 11, wherein the separation method is selected from the group consisting of centrifugation, filtration, and dialysis.

13. The method of claim 1, wherein during the illuminating step, the cells are presented as a thin layer of cells, wherein the thin layer is between 1.0 mm and 20 mm thick.

14. The method of claim 1, wherein at least 80% of the population of cells retaining the photosensitive compound is killed during the illuminating step.

* * * * *